United States Patent

Pruett et al.

[11] Patent Number: 4,775,760
[45] Date of Patent: Oct. 4, 1988

[54] DIBENZO[F,IJ]ISOQUINOLINE-2,7-DIONE DERIVATIVES

[75] Inventors: Wayne P. Pruett, Kingsport; Samuel D. Hilbert, Jonesborough; John G. Thompson; Max A. Weaver, both of Kingsport, all of Tenn.

[73] Assignee: Eastman Kodak Company, Rochester, N.Y.

[21] Appl. No.: 41,513

[22] Filed: Apr. 23, 1987

[51] Int. Cl.[4] .......................................... C07D 221/18
[52] U.S. Cl. .................................................. 546/76
[58] Field of Search ...................................... 546/76

[56] References Cited

U.S. PATENT DOCUMENTS 2,268,814  1/1942  Frame ............................. 540/76

FOREIGN PATENT DOCUMENTS 000832  1/1971  Japan ............................. 546/76
7483   of 1913  United Kingdom .

OTHER PUBLICATIONS

Cotton, ed, Advanced Inorganic Chemistry, 2nd ed., (1962) p. 560.

Primary Examiner—Donald G. Daus
Assistant Examiner—William A. Teoli, Jr.
Attorney, Agent, or Firm—John F. Stevens; William P. Heath, Jr.

[57] ABSTRACT

Novel substituted isoquinoline compounds of the formula

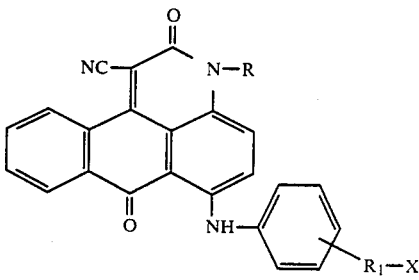

wherein
R is lower alkyl,
$R_1$ is lower alkylene, 1-3 lower alkyleneoxy groups or lower alkylenethio, and
X is one or more substitutents selected from the group consisting of hydroxyl, carbalkoxy, carboxy and acyloxy.

These novel substituted isoquinolines can be used as dyes, toners or color bodies, and in particular as toners for polyesters.

6 Claims, No Drawings

DIBENZO[F,IJ]ISOQUINOLINE-2,7-DIONE DERIVATIVES

FIELD OF THE INVENTION

This invention relates to novel substituted isoquinolines, processes for their manufacture, and their use as dyes, toners and color bodies.

BACKGROUND OF THE INVENTION

A desirable feature of polymer materials in many instances is an appearance of whiteness. For instance, it is often desired that fabrics manufactured from polyester fiber present the appearance of whiteness to the observer.

Unfortunately, native polyester fiber as manufactured has a yellowish appearance unacceptable to the observer.

At the present time, in order to improve the apparent whiteness in polyester materials, toners are incorporated into the polyester to hide the yellow color. Such toners usually have a visible absorption maximum in the range of 575 nm to 595 nm as measured in acetone.

Cobalt acetate is one of the most widely used toners in the industry to mask the yellow color of polymers. However, cobalt acetate has a number of disadvantages.

For instance, cobalt acetate toner materials tend to be unstable during storage as a result of temperature and humidity and undergo an undesirable color shift toward yellow. Hence, when high cobalt concentrations (70 ppm) are needed to mask the yellow color of some polymers there is a tendency to impart a gray color to the polymer.

Secondly, high cobalt concentrations are a concern to some regulatory agencies.

Thirdly, cobalt lowers polymer thermal stability and increases acetaldehyde formation in poly(ethylene terephthalate).

Lastly, cobalt has a strong tendency to form insoluble residues that collect on the interior walls of the reactor which leads to quality problems.

Thus, a real need is perceived to exist for a toner or dye which improves the apparent whiteness of polymers such as polyester which at the same time lacks the shortcomings that the are associated with prior art toners such as cobalt acetate.

SUMMARY OF THE INVENTION

A novel group of isoquinolines has been discovered which can be used as toners, dyes and colorants for polymers and the like without at the same time having the disadvantages that accompany many of the prior art toners, dyes and colorants.

The novel isoquinolines of the present invention are substituted 1-cyano-3H-dibenzo[f,ij]isozuinoline-2,7-diones having the following structural formula

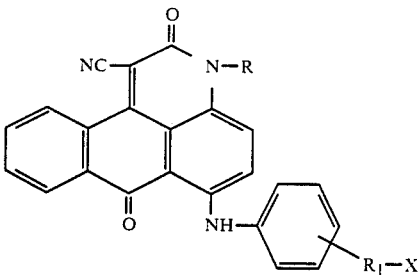

wherein

R is a lower alkyl;

$R_1$ is a lower alkylene, 1-3 lower alkyleneoxy groups or lower alkylenethio; and X is one or more substituents selected from the group consisting of hydroxyl, carbalkoxy, carboxy and acyloxy.

Illustrative of suitable R groups are alkyls of 1 to 8 carbon atoms such as methyl, ethyl, propyl, butyl, pentyl, hexyl, heptyl and octyl and isomers thereof.

Suitable groups for the substituent $R_1$ are methylene, ethylene, propylene, butylene, 1,4-tetramethylene, 1,5-pentamethylene, 1,6-hexamethylene, 1,7-heptamethylene and 1,8-octamethylene.

Suitable lower alkyleneoxy groups are methyleneoxy, ethyleneoxy, propyleneoxy, 1,4-tetramethyleneoxy, 1,5-pentamethyleneoxy, 1,6-hexamethyleneoxy, 1,7-heptamethyleneoxy and 1,8-octamethyleneoxy.

Illustrative of lower alkylenethio groups are methylenethio, ethylenethio, propylenethio, 1,4-tetramethylenethio, 1,5-pentamethylenethio, 1,6-hexamethylenethio, 1,7-heptamethylenethio, 1,8-octamethylenethio.

The X groups of the novel compounds are all esterifiable groups capable of reacting in an esterification of transesterification reaction to form an ester.

Preferred X groups include hydroxyl, carboxy and carbalkoxy such as carbomethoxy, carbethoxy, carbopropoxy, carbobutoxy, carbamyloxy, carbohexyloxy, carboheptyloxy, carboctyloxy, and their isomers.

When X is acyloxy, the acyl moiety is derived from any aliphatic or aromatic carboxylic acid of 1 to 20 carbon atoms. Typically, the preferred acyl moieties include those derived from formic acid, acetic acid, propionic acid, butyric aci, valeric acid, hexanoic acid, heptanoic acid, octanoic acid, benzoic acid, naphthanoic acid and isomers thereof.

In defining the foregoing groups for $R_1$ and X it is to be understood that these groups may contain one or more further substituents, such as halogen, alkoxy, cyano or amido groups which do not interfere with the novel characteristics of the compounds. The thus derivatized compounds are within the scope of this invention and the uses described herein.

Preferred isoquinolines of this invention are those having the formula

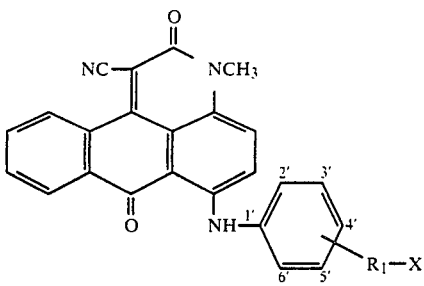

wherein —R₁X is —OCH₂CH₄OH, —CH₂CH₄OH or —CH₂OH, and is preferably positioned at the 4' or 3' position.

The compounds of the present invention may be prepared by a modified Ullmann reaction involving the nitrogen arylation of aniline in the presence of copper catalyst according to the reaction

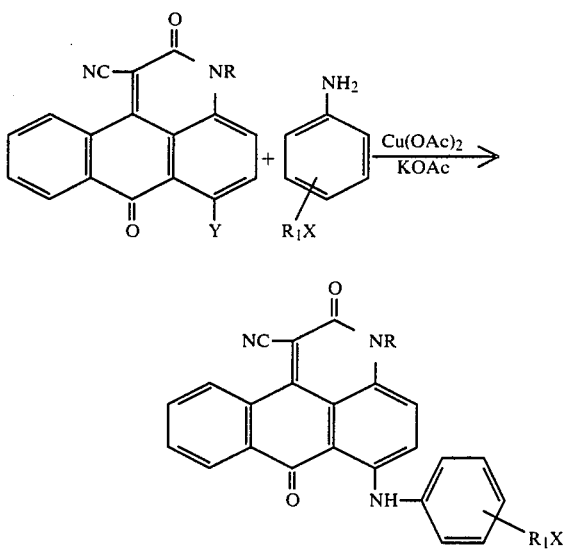

wherein

Y is halogen; and

R, R₁ and X are as defined hereinbefore.

Typically, the reaction is carried out in the presence of catalytic amounts of a copper salt and a suitable base. The halogen substituted dibenzoisoquinolinedione reacts with the aniline amino moiety forming the anilino derivative of the dibenzoisoquinolinedione which is recovered and purified by conventional techniques embodying solvent removal, filtration and recrystallization.

Of the foregoing reactants, the aniline compounds are well known and commercially available. The starting halogenated dibenzoisoquinolinediones are prepared, in general, by the following method as described by Allen, C. F. H., et al., JACS: 585–588 (1950).

An intermediate 1-amino-4 halogenoanthraquinone (I) is reacted with chloroacetyl chloride or chloroacetyl anhydride

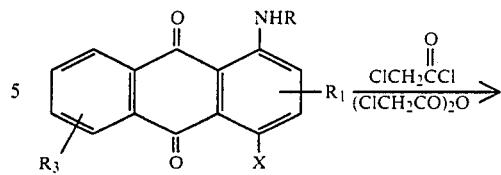

X = Cl, Br, etc.

I

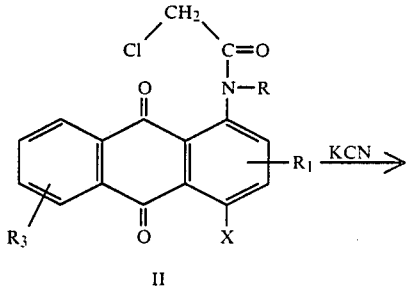

II

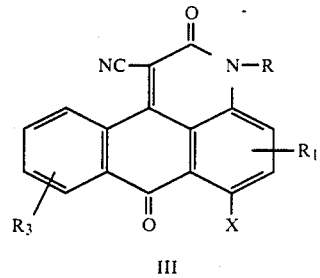

III to give 1-(chloroacetamido)-4-halogenoanthraquinone (II), which is ring closed to halogenated dibenzoisoquinolinedione (III) by treatment with an alkali metal cyanide such as potassium cyanide.

The compounds of the present invention are useful as dyes, toners and color bodies, either alone or in conjunction with other compounds.

The present compounds are particularly useful as toners for synthetic, semi-synthetic and natural polymeric materials.

Typical of these polymeric materials are the polycondensation products of bifunctional or polyfunctional compounds possessing condensable groups.

Illustrative of such polycondensation products are polyesters, especially saturated polyesters such as poly(ethyleneterephthalate) and polycarbonates formed by the polymerization of a diol and a carbonate ester or acid chloride.

Other polymeric materials with which the compounds may be used include semi-synthetic organic materials such as, for example, cellulose esters of varying degrees of esterification of regenerated cellulose.

Natural polymeric materials in which the compounds of this invention may find use include those based on cellulose, proteins, cotton, wool, linen, silk and the like.

The substituted cyanodibenzoisoquinolinedione compounds of this invention may be incorporated into polyesters either by copolymerization during the polycondensation reaction or by admixture with the polyester polymer. The esterifiable reaction group in the toner compound of the invention will cause the compound to function as a chain terminating group when added during the polyester condensation reaction.

The toner compound will be incorporated in the polyester structure as a terminal group on the polyester molecule. Thus, the toner molecule is bonded to the polymer molecule through the primary valence forces of an ester bond.

Alternatively, the compounds of the invention may be incorporated into the polyester by simply mixing the compound into the polyester, by melt mixing using conventional apparatus such as a two roll mill, or by mixing with the molten polyester during fiber spinning operations.

A distinguishing feature of the polyesters of the present invention incorporating the compounds described herein is that the compounds added either as part of the polymer structure or as mixtures thereto do not degrade the desirble physical and chemical properties of polyester materials.

It is a common problem that the inclusion of a comonomer or a chain terminating compound in a polyester polymerization reaction may adversely affect the physical properties of the polymer such as the melting point or the tensile strength of the polyester.

It is well known that chain terminators, by the mere mechanism of their reaction, lower the average molecular weight of the polymer system, leading to less than maximum physical and chemical properties for the polyesters derived therefrom.

The cyanodibenzoisoquinolinedione compounds of the invention effectively improve the apparent whiteness of polyesters even when incorporated into the polyester in very small amounts. Thus, good results are obtained even with amounts of less than 10 parts per million of the inventive compounds based on the weight of polyester.

Consequently, when the present compounds are added in such small amounts, they have a negligible effect on the average molecular weight of the polyester and on the physical and chemical properties associated therewith.

In other words, the compounds of the invention have as an inherent part of their chemical structure the ability to provide polyesters with an aborptivity which is sufficiently strong to confer apparent whiteness to the polyester polymer even when employed in very small amounts.

Other objects, advantages and features of the present invention will become apparent to those skilled in the art from the following discussion.

DESCRIPTION OF THE PREFERRED EMBODIMENTS

Among the polyesters and copolyesters useful in the instant invention are those resulting from reacting one or more of the glycols of the series $HO(CH_2)_nOH$, wherein n is an integer from 2 to 10, cycloaliphatic glycols, with one or more dicarboxylic acids or ester-forming derivatives thereof.

Among the dicarboxylic acids and ester-forming derivatives thereof which are useful in the present invention there may be named terephthalic acid, isophthalic acid, 2,6-naphthalenedicarboxylic acid, p,p'-dicarboxydiphenyl, p,p'-dicarboxydiphenylsulphone, p,p'-dicarboxyldiphenylmethane, 1,4-cyclohexanedicarboxylic acid, 1,3-cyclohexanedicarboxylic acid, succinic acid, glutaric acid, adipic acid, 1,12-dodecanedioic acid and alphatic and aryl esters, half esters and acid halides of the above named compounds.

Examples of the polyhydric alcohols which may be employed in practicing the instant invention are ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, diethylene glycol, triethylene glycol, dipropylene glycol, tripropylene glycol and x,8-bis(hydroxymethyl)tricyclo[5.2.1.0]-decane wherein x represents 3, 4, or 5.

The incorporation of the present toners into a polyester composition is described in co-filed U.S. patent application Ser. No. 41,512 by the present inventors under the title "Polyesters Having an Improved Whiteness". The entire content of the co-filed application is incorporated herein by reference.

The following illustrates one preferred method of preparing polyesters incorporating toners of the instant invention.

Dimethylterephthalate, one or more glycols such as ethylene glycol, suitable catalysts and less than 10 parts per million of a toner of this invention are charged to a reactor and heated at between about 200° C. and 225° C. for approximately 140 minutes under a nitrogen atmosphere.

This first stage of the transesterification reaction produces the bisglycolate of terephthalic acid which, without further separation, is employed in the second stage to produce the polyester.

After the ester interchange reaction catalyst-inhibitor comprising a phosphate ester is added to the reaction product of the reaction product is polycondensed. The preferred phosphate ester has the formula

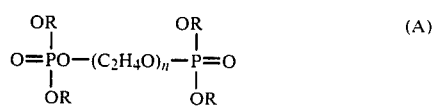

wherein
n has an average value of 1.5 to about 3.0, with about 1.8 being most preferred; and
each R is hydrogen or alkyl having from 6 to 10 carbon atoms, with octyl being most preferred, the ratio of the number of R groups of hydrogen atoms to the number of phosphorus atoms being about 0.25 to 0.50 with about 0.35 being most preferred; and the ester having a free acidity equivalent of about 0.2 to 0.5, the ester being present in the amount to provide phosphorus in the amount of 13–240 parts per million based on the acid fraction of the polyester to be produced. Other phosphate esters useful in this invention include ethyl acid phosphate, diethyl acid phosphate, triethyl acid phosphate, arylalkyl phosphates, tris-2-ethylhexyl phosphate and the like. Preferred phosphate esters are those disclosed in U.S. Pat. No. 3,962,189.

In the second stage, the reaction is conducted at reduced pressures. Pressures are maintained within about 0.2 or 0.5 millimeters of mercury to allow polycondensation to take place at a temperature of approximately 278° C.

The reduced pressure is necessary to remove the free polyhydric alcohol which is volatilized under these conditions and removed from the system. The polyester resulting from the polymerization process is water clear with a desirable, very slight blue tint as compared to a polyester prepared without a blue toner which exhibits an undesirable yellow color.

In addition to exhibiting improved apparent whiteness, the thus prepared polyesters are found to be stable to heat under polymerization conditions, stable to light and other environmental effects and to impart no abrasive characteristics to the polymers in which they are incorporated.

Having now generally described this invention, the same will be better understood by reference to certain specific examples, which are included herein for purposes of illustration only and are not intended to be limiting of the invention or any embodiment thereof, unless so specified.

The following examples illustrate the methods used to prepare the compounds of the present invention and the methods used to incorporate those compounds into polymeric materials, and in particular, into polyesters.

EXAMPLES

Example 1

Preparation of 1-cyano-6-[4'-(2-hydroxyethyl)anilino]-3-methyl-3H-dibenzo[f,ij]isoquinoline-2,7-dione A mixture of 6-bromo-1-cyano-3-methyl-3H-dibenz[f,ij]isoquinoline-2,7-dione (2.0 ), p-aminophenylethanol (15 g), potassium acetate (2.0 g), cupric acetate (0.2 g), and butanol (10 mL) is heated gradually to about 80° C., held for 5–10 minutes, and then drowned into 250 mL of 10% HCl.

The solid product is collected by filtration, washed with water, dried in air, and recrystallized twice from nitrobenzene to remove red impurities and traces of starting material.

A yield of 0.65 g of product is obtained. The product has a visible absorption maximum at 587 nm in acetone, and imparts a reddish-blue color to the acetone. The structure of the compound is as follows.

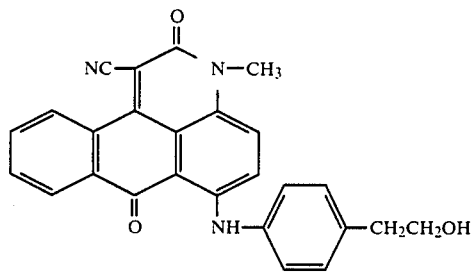

Example 2

Preparation of 1-cyano-6-[4'-(2-hydroxyethoxy)anilino]-3-methyl-3H-dibenzo[f,ij]isoquinoline-2,7-dione A mixture of 6-bromo-1-cyano-3-methyl-3H-dibenzo[f,ij]isoquinoline-2,7-dione (2.0 g), p-aminophenoxyethanol (10.0 g), potassium acetate (2.0 g), cupric acetate (0.5 g), and n-butanol (25 mL) is heated and stirred at steam bath temperature for 1 hour.

The warm reaction mixture is drowned into acetone (200 mL) and the solid collection by filtration, washed with acetone, and slurried in 150 mL of 10% HCl at about 60° C. with stirring.

After being collected by filtration, the dye is washed with hot water and then methanol. This is followed by drying in air.

Recrystallization from nitrobenzene yields 0.6 g of essentially pure blue toner having the following structure.

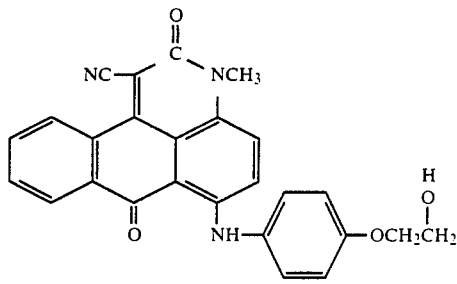

Example 3

Preparation of Poly(ethylene terephthalate) Copolymerized With 30 Mole % 1,4-cyclohexanedimethanol and 4 ppm of 1-cyano-6[4'-(2-hydroxyethoxy)anilino]-3-methyl-3H-dibenzo[f,ij]isoquinoline-2,7-dione Blue Toner The compounds below are placed in a 500 mL, single-necked, round-bottom flask.

97 g (0.5 m) dimethyl terephthalate, 23 g (0.16 m) 1,4-cyclohexanedimethanol (70% trans isomer), 52.1 g (0.64 m) ethylene glycol, 0.22 mL of an n-butanol solution of acetyl triisopropyl titanate containing 0.0066 g titanium, 1.25 mL of an ethylene glycol solution of $Mn(OCOCH_3)_2 \cdot 4H_2O$ containing 0.006 g manganese, and 4 mL of an acetone solution containing 0.000436 g (4 ppm) o 1-cyano-6[4'-(2-hydroxyethoxy)anilino]-3-methyl-3H-dibenzo[f,ij]isoquinoline-2-7-dione blue toner.

The flask is equipped with a nitrogen inlet, metal stirrer, vacuum outlet and condensing flask. The flask and contents are heated at 200° C. in a Belmont metal bath for 60 minutes and at 225° C. for 80 minutes with a nitrogen sweep over the reaction mixture while the ester interchange takes place.

After the ester interchange reaction, the phosphate ester (A) described above is added to the reaction product in an amount that provides phosphorus in an amount of about 125 parts per million based on the final theoretical polymer weight and the reaction product is polycondensed.

The metal bath temperature is increased to 278° C.

Vacuum is then applied to the flask and the flask and contents are heated at 278° C. for 60 minutes under a pressure of about 0.2 to 0.5 mm Hg to allow polycondensation to take place.

The flask is removed from the metal bath and allowed to cool in a nitrogen atmosphere. The resulting amorphous polymer is water clear with a desirable, very slight blue tint (the polyester prepared with no blue toner is yellow colored).

The reulting polymer has an inherent viscosity of 0.77 when measured in a 60/40 ratio by weight of phenol-tetrachloroethane at a concentration of 0.5 g per 100 mL. Gas chromatographic analyses of a hydrolyzed sample of the polyester show that the polyester contains 30 mol % of 1,4-cyclohexanedimethanol.

Example 4

Preparation of Poly(1,4-cyclohexylenedimethylene terephthalate) Copolymerized With 37 Mole % Ethylene Glycol and 4 ppm of 1-Cyano-6-[4'-(2hydroxyethyl)anilino]-3-methyl-3H-dibenzo[f,ij]isoquinoline-2,7-dione Blue Toner The compounds below are placed in a 500 mL, single-necked, round-bottom flask.

97 g (0.5 m) dimethyl terephthalate, 49 g (0.34 m) 1,4-cyclohexanedimethanol (70% trans isomer), 40.9 g (0.66 m) ethylene glycol, 0.25 mL of a n-butanol solution of acetyl triisopropyl titanate containing 0.0075 g titanium, 1.42 mL of an ethylene glycol solution of Mn $(OCOCH_3)_2.4H_2O$ containing 0.0068 g manganese, and 4.5 mL of an acetone solution containing 0.0004905 g (4 ppm) of 1-cyano-6-[4'-(2-hydroxyethyl)-anilino]-3-methyl-3H-dibenzo[f,ij]isoquinoline-2,7-dione blue toner.

The polymerization is carried out as in Example 3 above.

The resulting amorphous polymer is water clear with a desirable very light blue tint (the polyester prepared with no blue toner is yellow colored). The resulting polymer has an inherent vicosity of 0.97. Gas chromatographic analyses of a hydrolyzed sample of the polyester show that the polyester contains 37 mol % ethylene glycol.

The invention now being fully described, it will be apparent to one of ordinary skill in the art that many changes and modifications can be made thereto without departing from the spirit or scope of the invention as set forth herein.

We claim:

1. A compound having the following structure:

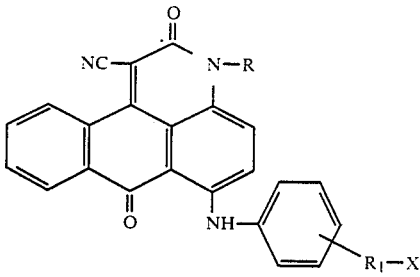

wherein
R is lower alkyl;
$R_1$ is lower alkylene, 1–3 lower alkyleneoxy or lower alkylenethio;
X is one or more substitutents selected from hydroxyl, carbalkoxy, carboxy, and acyloxy.

2. The compound according to claim 1, wherein $R_1$ is selected from the group consisting of methylene, ethylene, propylene, butylene, 1,4-tetramethylene, 1-5-pentamethylene, 1,6-hexamethylene, 1,7-heptamethylene, 1,8-octamethylene, methyleneoxy, ethyleneoxy, propyleneoxy, 1,4-tetramethyleneoxy, 1,5-pentamethyleneoxy, 1,6-hexamethyleneoxy, 1,7-heptamethyleneoxy, 1,8-octamethyleneoxy, methylenethio, ethylenethio, propylenethio, 1,4-tetramethylenethio, 1,5-pentamethylenethio, 1,6-hexamethylenethio, 1,7-heptamethylenethio, and 1,8-octamethylenethio.

3. The compound according to claim 1, wherein X is selected from the group consisting of carbomethoxy, carbethoxy, carbopropoy, carbobutoxy, carbamyloxy, carbohexyloxy, carboheptyloxy, carboctyloxy, formyl, acetyl, propionyl, butyryl and valeryl.

4. The compound according to claim 1, wherein R is methyl; and
$R_1X$ is 4—$OC_2H_4OH$.

5. The compound according to claim 1, wherein R is methyl; and
$R_1X$ is 4—$C_2H_4OH$.

6. The compound according to claim 1, wherein R is methyl; and
$R_1X$ is 3—$CH_2OH$.

* * * * *